United States Patent [19]

Cullo et al.

[11] Patent Number: 4,962,272
[45] Date of Patent: Oct. 9, 1990

[54] TREATMENT OF ARSINE REMOVAL CATALYSTS

[75] Inventors: Leonard A. Cullo, Hempfield Township, Westmoreland County; Edward F. Restelli, Jr., Oakmont Boro, both of Pa.

[73] Assignee: Aristech Chemical Corporation, Pittsburgh, Pa.

[21] Appl. No.: 358,287

[22] Filed: May 30, 1989

[51] Int. Cl.$^5$ .................... C07C 7/12; B01J 38/04; B01J 23/82; B01D 53/02
[52] U.S. Cl. ........................... 585/826; 55/74; 502/34; 502/55; 585/820
[58] Field of Search ............... 502/34, 55, 56; 585/820–826; 423/87, 210; 55/74

[56] References Cited

U.S. PATENT DOCUMENTS

| 3,050,571 | 8/1962 | Fleming et al. | 260/677 |
| 3,782,076 | 1/1974 | Carr et al. | 55/74 |
| 3,812,652 | 5/1974 | Carr et al. | 55/68 |
| 4,009,009 | 2/1977 | Massoth et al. | 55/73 |
| 4,044,067 | 8/1977 | Besozzi et al. | 260/680 E |
| 4,083,924 | 4/1978 | Styring | 502/34 |
| 4,150,063 | 4/1979 | Besozzi et al. | 260/680 E |
| 4,227,025 | 10/1980 | Montgomery | 585/259 |
| 4,444,987 | 4/1984 | Brownell et al. | 585/850 |
| 4,593,148 | 6/1986 | Johnson et al. | 585/823 |
| 4,605,812 | 8/1986 | Nowack et al. | 585/845 |
| 4,613,724 | 9/1986 | Debras et al. | 585/824 |
| 4,849,577 | 7/1989 | Boitiaux et al. | 585/520 |
| 4,861,939 | 8/1989 | Debras et al. | 585/823 |

*Primary Examiner*—Paul E. Konapka
*Attorney, Agent, or Firm*—William L. Krayer

[57] ABSTRACT

Supported metal oxide catalysts such as lead oxide catalysts are rejuvenated after absorbing arsenic compounds from hydrocarbon steams (such as propylene) by heating them in an inert, oxygen-free atmosphere, optionally with moisture present.

21 Claims, No Drawings

TREATMENT OF ARSINE REMOVAL CATALYSTS

TECHNICAL FIELD

This invention relates to the purification of hydrocarbon streams such as propylene and especially to the removal of arsenic compounds from them, preferably after the removal of carbonyl sulfide. Most particularly, this invention relates to the rejuvenation of a supported lead oxide or other metal oxide or mixed oxide catalyst after it has accumulated designated levels of arsenic compounds.

BACKGROUND ART

Propylene and other lower olefins used in polymerization processes must be free of contaminants which poison the polymerization catalysts and/or otherwise distort the polymerization process. A contaminant which has received particular attention for propylene purification is carbonyl sulfide; since carbonyl sulfide tends to vary considerably within a range of small concentrations in propylene, it is particularly difficult to contend with and its removal has accordingly been the subject of a number of patents. See, for example, U.S. Pat. Nos. 4,613,724 and 4,444,987.

The arsenic compound of principal concern in propylene purification applications is most commonly arsine since it is the most volatile form of arsenic and also boils at a temperature close to the boiling point of propylene. However, other forms of arsenic may also be present and reference to arsenic herein is intended to include arsine and all other forms of arsenic that may be present in the process stream. The arsenic is removed by reacting or complexing with the metal oxide or oxides contained in the catalyst. The terms "removal" and "adsorption" of arsenic by the catalyst as used in this disclosure implies that such reacting or complexing occurs. Such complexing results in more complete removal of the arsenic contaminant than conventional adsorption processes would permit.

In U.S. Pat. No. 4,009,009 the use of a lead oxide catalyst on an alumina support is suggested for the removal of COS from propylene; in U.S. Pat. No. 3,782,076 a similar lead oxide containing catalyst is suggested for the removal of arsine from hydrocarbons. Arsine has been found to be a particularly unpredictable contaminant in both concentration and effect. The removal of arsine ($AsH_3$) is attendant with additional difficulties, however, in that its infamous reputation as a poison requires that it be disposed of in a prudent manner. The process of U.S. Pat. No. 3,782,076 has not conclusively addressed this problem.

The present invention is an improvement on U.S. Pat. No. 3,782,076 wherein a lead oxide catalyst on an alumina support is used to remove arsenic compounds from hydrocarbon streams. The present invention is a practical and efficient method of activating lead oxide catalysts and other supported metal oxide catalysts having been used to remove arsine and/or other arsenic compounds from hydrocarbon steams, particularly lower olefins and, more particularly, propylene.

U.S. Pat. No. 3,812,652 by Carr suggests regenerating the spent arsenic removal catalyst by contact with a gas stream containing free molecular oxygen. Air is cited as an example of such a gas stream. However, in some process applications such as propylene polymerization, the use of oxygen in the system in highly undesirable. Therefore, to apply the teachings of U.S. Pat. No. 3,812,652, the guard bed catalyst must be removed from the system and processed externally. U.S. Pat. No. 4,593,148 also teaches the use of air for catalyst regeneration and thereby suffers the same disadvantage as U.S. Pat. No. 3,812,652.

The reader may also be interested in U.S. Pat. Nos. 4,593,148, 4,605,812, 4,442,077, 4,088,734, 4,044,067, 4,150,063, and 4,613,724, all of which remove either COS or arsine, or both, from hydrocarbons. Generally, the catalysts are either not regenerated or are regenerated with oxygen or air. The regeneration process tends to be somewhat complicated by the fact that in most of the cases, the removal of arsine takes place along with the removal of sulfur compounds such as carbonyl sulfide. Thus, regeneration of the catalyst tends to be dominated by the process of removing the sulfur, and the arsenic, being present in generally smaller quantities, is necessarily subject to the same regenerative process, which may not be particularly advantageous for arsenic removal. An additional complication is the fact that lead oxide reacts irreversibly, for practical purposes, with sulfur—thus, where a lead oxide catalyst is used on a stream which contains both arsine and sulfur-containing compounds, it suffers from the dual problem that arsine pickup may be interfered with and there may be a drastic diminishing of the ability to be regenerated. It should be noted that the inventors in U.S. Pat. No. 3,782,076 recognize (col. 3, lines 16-28) that arsine removal is more efficient when sulfur compounds have been previously removed from the subject gas.

We have developed a novel process for the purification of hydrocarbon steams which includes a new process for the rejuvenation of a supported metal oxide or mixed oxide catalyst loaded with arsenic.

The experimentation performed in support of this disclosure suggest that the total capacity of the supported oxide catalyst for arsenic removal may be is limited by the catalyst composition and the stiochiometry of the reaction. Since in our procedure we do not actually remove arsenic from the combined catalyst and its support, but enable it to achieve its maximum loading, the regeneration of the catalyst which we accomplish is in reality a rejuvenation and is referred to as such herein. In most instances, it is economically advisable to rejuvenate the supported metal oxide or mixed oxide catalyst rather than to replace it. It is also advantageous to perform this rejuvenation in situ rather than incurring the additional expense and down time associated with emptying the reaction vessel and performing the procedure off-line. Disclosure of the Invention The supported metal oxides or mixed oxides to which this disclosure applies are those which complex or react with arsenic compounds and particularly arsine at temperatures below 300° C. and preferably below 100° C. The literature reports that copper oxide, copper chromite, copper oxide-zinc oxide, and lead oxide catalysts will remove arsenic compounds from hydrocarbon feed; see U.S. Pat. Nos. 3,782,076, 3,789,581, 3,812,652, 4,605,812, and 4,593,148. The reference cited suggest that the catalysts be operated at from 80° to 150° F.

Our invention includes rejuvenation of arsenic-containing catalysts of the above description and/or any other oxide or mixed oxides used for this purpose. The basic utility of this invention is that the procedures specified do not admit any toxic materials to the atmosphere and thereby have no environmental impact. The procedures specified require no air or oxygen and are therefore safe to practice in explosive atmospheres. These procedures may be performed on the catalysts in situ thereby eliminating the lost operating time and expense which accompanies any catalyst treatment performed off-line. Lastly, this invention greatly extends the catalyst life.

We have found that spent supported metal oxide catalysts used for arsine removal may be rejuvenated [provided the amount of arsenic in the catalyst has not reached the adsorption limit of the catalyst] by heating same in an inert gas stream or in an inert atmosphere at a temperature from 50° to 400° C. and preferably from 100° to 400° C. for a period of at least about ½ hour and preferably from 1 to 100 hours. Processing beyond this time will generally not improve results commensurate with the additional effort required. Said catalysts may also be rejuvenated by heating same in a stream of wet inert gas at a GHSV of at least about 100 and at a temperature from 50° to 400° C. and preferably from 100° to 400° C. for a period of at least about ½ hour and preferably from 1 to 50 hours with the moisture content of the inert gas is being from 0.001 to 80 mol percent and preferably from 0.01 to 20 mol percent. Processing beyond this time will generally not improve results commensurate with the additional effort required. Those skilled in the art of process engineering can adjust moisture content of the inert gas stream in correspondence with the process conditions used to accomplish the desired extent of catalyst rejuvenation. Said catalysts may also be rejuvenated by heating same in a steam environment at from 100° to 400° C. for a period of at least about ½ hour and preferably from 1 to 50 hours. Processing beyond this time will generally not improve results commensurate with the additional effort required. Said catalysts may be rejuvenated by adding from 0.1 to 50% moisture and preferably from 1 to 15% moisture to the catalyst and heating same in an inert gas stream or in an inert gas atmosphere at from 50° to 400° C. and preferably from 100° to 400° C. for a period of at least about ½ hour. Again, while processing in excess of 50 hours is not harmful, little if any additional benefit may be expected by doing so.

In one aspect, our invention is a process for the rejuvenation of a supported metal oxide such as a lead oxide catalyst having been used for the adsorbtion of arsenic, wherein the loaded catalyst is treated by one of the procedures described above. The catalyst should be on a porous base or support, preferably, but not limited to, an inorganic oxide material substantially comprising either one metal oxide or a mixture of oxides, carbides, silicates or aluminates; in either case, the type of support commonly used in preparing catalysts and familiar to those skilled in the art such as, but not limited to, alumina, silica, silica-alumina, magnesia, silica magnesia, calcium aluminates, calcium silicates, zinc oxide and silicon carbide. In another aspect, our invention is a sequence of purification steps for propylene and other lower olefins wherein the lower olefin is passed through a catalyst bed specifically adapted for the removal of carbonyl sulfide and subsequently passed through a bed of supported lead oxide catalyst for the removal of arsine. The arsine removal catalyst bed, free of sulfur, is then subjected to one of the rejuvenation treatments described above.

The invention will be discussed and described with reference to certain experiments and data in the following paragraphs.

For the studies of this work, the catalysts were first sized to −35, +45M unless otherwise stated and tested in a micro reactor system. To define capacity of the supported mixed oxides for oxides for removal of arsenic compounds, the catalysts were contacted at a room temperature of approximately 75° F. with a nitrogen stream containing approximately 20 ppm arsine at a GHSV of approximately 2000. Arsine levels in the feed gas and reactor effluent were measured semi-quantitatively using Drager tubes and quantitatively using a GC with a photoionization detector. Detection level of this system was about 30 ppb. Saturation of the catalysts with complexed arsenic was considered to occur when arsine level in the reactor effluent reached approximately 0.2 ppm.

The catalysts saturated with arsine were then rejuvenated according to our invention as described below. An experiment was also performed with unsupported lead oxide as the catalyst to show the ineffectiveness of straight oxidation and the necessity of a substrate to rejuvenate the catalyst.

While the arsenic removal experiments of this work were performed in the vapor phase, the rejuvenation procedures specified in this disclosure would be the same for supported oxide beds operating on both liquid and vapor process streams.

EXAMPLE 1:

One half gram of unsupported lead oxide powder was charged to the micro reactor and contacted with a stream of nitrogen containing 20 ppm arsine at a GHSV of approximately 3200. The lead oxide adsorbed 0.53 weight percent As before arsine breakthrough. The lead oxide was then heated for 3 hours at 204° C. and again contacted with the nitrogen feed containing 20 ppm arsine. No adsorption of arsine by the lead oxide occurred, showing that the unsupported PbO had not been rejuvenated. The lead oxide was then heated in an air stream flowing at approximately 3200 GHSV for 3 hours at 204° C. and again contacted with the nitrogen feed containing 20 ppm arsine. No further adsorption of arsenic by the unsupported PbO occurred.

EXAMPLE 2:

One-half gram of a catalyst having a composition of about 20% PbO on an alumina substrate and having a moisture content of 5% was contacted with a stream of nitrogen containing 20 ppm arsine at a GHSV of approximately 2000. The catalyst adsorbed 0.78% As before arsine breakthrough occurred. The catalyst was then heated for 3 hours at 204° C. and again contacted with the nitrogen feed containing 20 ppm arsine. After the rejuvenation treatment, the catalyst adsorbed an additional 1.42% As.

EXAMPLE 3:

The catalyst of Example 2, now having an arsenic content of 2.18% and having just experienced arsine breakthrough was then heated for 3 hours at 203° C. in a stream of nitrogen at a GHSV of approximately 2000 with the nitrogen containing 3.2 mol percent water, produced by saturating the nitrogen stream at 25° C. and 740 mm total pressure. In this treatment, water in the amount of 5.4% by weight of the catalyst was passed into the reactor. The rejuvenated catalyst was then contacted with nitrogen containing 20 ppm arsine at a temperature of 75° F. and GHSV of approximately 2000. The catalyst then adsorbed 1.14% by weight arsenic before arsine breakthrough occurred.

EXAMPLE 4:

One-half gram of a catalyst having a composition of about 20% PbO on an alumina substrate, initially containing 5% water and containing 3.75% by weight arsenic, and having just experienced arsine breakthrough was heated in a stream of dry nitrogen for 3 hours at 203° C. at a GHSV of approximately 2000. After this treatment, the catalyst was then contacted with nitrogen containing 20 ppm arsine at a temperature of 75° F. and GHSV of approximately 2000. The catalyst then adsorbed 0.14% by weight additional arsenic after which arsine breakthrough occurred.

EXAMPLE 5:

The catalyst of Example 4 now having an arsenic content of 3.89% and having just experienced arsine breakthrough was then rejuvenated by heating for 3 hours at 203° C. in a stream of nitrogen at a GHSV of approximately 2000 with the nitrogen containing 3.3 mol percent water, produced by saturating the nitrogen stream at 25° C. and 730 mm total pressure. The rejuvenated catalyst was contacted with nitrogen containing 20 ppm arsine at a temperature of 75° F. and GHSV of approximately 2000. The catalyst then adsorbed 0.42% by weight additional arsenic before arsine breakthrough occurred.

EXAMPLE 6:

The catalyst of Examples 4 and 5, having 4.34% by weight arsenic, and having just experienced arsine breakthrough was rejuvenated by heating for 3 hours at 300° C. in a stream of nitrogen at GHSV of approximately 2000 with the nitrogen containing 0.033 mol percent water, produced by saturating the nitrogen stream at 25° C. and 730 mm total pressure. The rejuvenated catalyst was contacted with nitrogen containing 20 ppm arsine at a temperature of 75° F. and GHSV of 2000. The catalyst then adsorbed 0.32% by weight additional arsenic before arsine breakthrough occurred.

During several of the rejuvenation procedures described above, the effluent stream from the reactor was analyzed periodically for arsine using an AID chromatograph. In all instances, no arsine was detected, showing that the rejuvenation procedure specified in this disclosure for supported metal oxide catalysts does not result in the release of volatile arsenic from the catalyst.

EXAMPLE 7:

One-half gram of a catalyst having a composition of about 20% PbO on an alumina substrate and being essentially dry was contacted with a stream of nitrogen containing 20 ppm arsine at a GHSV of approximately 2000. The catalyst adsorbed about 3.04% As before arsine breakthrough occurred. The catalyst was then heated for 3 hours at 204° C. in a steam atmosphere and again contacted with the nitrogen feed containing 20 ppm arsine. After the rejuvenation treatment, the catalyst adsorbed about an additional 4.47% As.

EXAMPLE 8:

One tenth gram of a catalyst having a composition of about 40% CuO and 40% ZnO with 20% $Al_2O_3$ diluted with four tenths gram of borosilicate glass beads ground to −35, +45M and being essentially dry was contacted with a stream of nitrogen containing 20 ppm arsine at a GHSV of approximately 2000. The catalyst adsorbed about 19.4% As before arsine breakthrough occurred. The catalyst was then heated for 3 hours at 204° C. in a steam atmosphere and again contacted with the nitrogen feed containing 20 ppm arsine. After the rejuvenation treatment, the catalyst adsorbed an additional 9.3% As.

EXAMPLE 9:

0.05 gram of a catalyst having a composition of about 10% CuO on an alumina substrate diluted with 0.45 grams borosilicate glass beads and being essentially dry was contacted with a stream of nitrogen containing 20 ppm arsine at a GHSV of approximately 2000. The catalyst adsorbed 3.80% As before arsine breakthrough occurred. The catalyst was then heated for 3 hours at 204° C. in a steam atmosphere and again contacted with the nitrogen feed containing 20 ppm arsine. After the rejuvenation treatment, the catalyst adsorbed an additional 2.10% As.

EXAMPLE 10:

0.05 gram of a catalyst having a composition of about 10% CuO with about 1% additional nickel, cobalt and maganese oxides on an alumina substrate diluted with 0.45 gram borosilicate glass beads and being essentially dry was contacted with a stream of nitrogen containing 20 ppm arsine at a GHSV of approximately 2000. The catalyst adsorbed 6.14% As before arsine breakthrough occurred. The catalyst was then heated for 3 hours at 204° C. in a steam atmosphere and again contacted with the nitrogen feed containing 20 ppm arsine. After the rejuvenation treatment, the catalyst adsorbed an additional 1.52% As.

It may be seen from the above that the rejuvenation process for arsenic-saturated metal oxide catalysts and particularly lead oxide catalysts on alumina or other supports and saturated with arsine or other arsenic includes passing an oxygen-free inert gas through the spent catalyst at a GHSV of greater than 50 for a period of at least one-half hour and preferably about one hour to about 100 hours, where the catalyst has absorbed arsenic in an amount up to about 35% of the contained lead oxide, the rejuvenating gas and catalyst bed being at a temperature at least about 50° C. and preferably about 100° to about 400° C. during the rejuvenation. Temperatures greater than 400° C. are at least partially effective for rejuvenation, but will run the risk of volatilizing arsenic. When the catalyst contains about 18% to about 24% PbO, several such rejuvenations may be conducted before the procedure becomes ineffectual. Specifically, it has been found that a PbO - on-alumina catalyst having about 18–24% PbO may accumulate from 4.6% to greater than 7% arsenic, depending on the initial condition of the catalyst, (after several rejuvenations as recited above) before it reaches a saturated state where further rejuvenations do not significantly increase the arsine level that the catalyst can adsorb.

While a complete rejuvenation will very likely not be accomplished by the use of our process for only one-half hour at 50° C., at least some rejuvenating effect may be observed.

The nitrogen or other oxygen-free gas may contain up to about 80 mole percent moisture, and in fact, as demonstrated above, the rejuvenating atmosphere may consist essentially of steam. Our invention is particularly useful in the removal of arsenic from lower olefins, i.e., ethylene, propylene and butene, and will be especially effective when it is preceded by a step for the removal of carbonyl sulfide by methods already known in the art. Thus, our invention includes a process for the purification of $C_{2-4}$ olefins comprising removing carbonyl sulfide therefrom, thereafter passing said olefins through a bed of metal (preferably lead) oxide catalyst to remove arsenic compounds, and thereafter rejuvenating the metal oxide catalyst by the method described herein.

Our invention alleviates the problem of disposing of the toxic arsenic-containing spent catalyst, in that it enables one to minimize the handling of the spent catalyst, i.e., instead of disposing of the catalyst after a first pass, as many rejuvenations as desired or as practical may be conducted without any arsine is actually being removed from the catalyst before the catalyst must be discarded.

We claim:

1. Method of rejuvenating a metal oxide or mixed metal oxide catalyst supported on a porous support, which catalyst has accumulated arsenic thereon, comprising passing through said catalyst an oxygen-free inert gas including up to about 80 mole percent moisture at a temperature of at least about 50° C. for at least one-half hour.

2. Method of claim 1 wherein the temperature is at least 100° C.

3. Method of claim 1 wherein the rejuvenation is conducted for about one hour to about 100 hours.

4. Method of claim 1 wherein the metal oxide is lead oxide.

5. Method of claim 1 wherein the metal oxide is copper oxide.

6. Method of claim 1 wherein the metal oxide comprises copper oxide, zinc oxide and aluminum oxide.

7. Method of claim 1 wherein the arsenic is in the form of arsine.

8. Method of claim 1 wherein the oxygen-free inert gas is nitrogen.

9. Method of claim 1 wherein the oxygen-free inert gas is steam.

10. Method of claim 1 wherein the oxygen-free inert gas includes about 0.01 to about 20 mole percent moisture.

11. Method of claim 1 wherein the catalyst contains about 0.1% to about 50% water by weight.

12. Method of claim 1 wherein the catalyst contains about 1% to about 15% moisture by weight.

13. Method of removing arsenic from a lower olefin comprising passing said lower olefin through a supported lead oxide catalyst until the potential of the catalyst for arsenic adsorption is diminished, rejuvenating said catalyst by heating it at a temperature of about 50° C. to about 400° C. in an oxygen-free inert atmosphere so as to enhance the potential of the catalyst for adsorbing arsine without passing any arsine outside the catalyst or its support, and thereafter again passing lower olefin through said catalyst.

14. Method of claim 13 wherein a plurality of rejuvenation steps are performed.

15. Method of claim 13 wherein the lower olefin is propylene.

16. Method of claim 13 wherein the lead oxide is on an alumina support and is present on it in an amount from about 18% to about 24%.

17. Method of claim 14 wherein each rejuvenating step takes place for a period of at least an hour.

18. Method of claim 13 wherein the inert atmosphere is nitrogen.

19. Method of claim 18 wherein the nitrogen contains about 1% to about 15% moisture.

20. Method of claim 13 wherein the atmosphere is steam.

21. Method of maintaining a lead oxide catalyst on alumina which is used for removing arsine from a lower olefin selected from ethylene propylene and butene comprising periodically rejuvenating said catalyst by passing an oxygen-free gas through it at a temperature of at least about 50° C. to distribute said arsine throughout said alumina, until the catalyst has accumulated at least about 4.6% arsine.

* * * * *

UNITED STATES PATENT AND TRADEMARK OFFICE
CERTIFICATE OF CORRECTION

PATENT NO. : 4,962,272

DATED : October 9, 1990

INVENTOR(S) : Leonard A. Cullo and Edward F. Restelli, Jr.

It is certified that error appears in the above-identified patent and that said Letters Patent is hereby corrected as shown below:

Column 1, line 48, change "(Ash$_3$)" to -- (AsH$_3$) --.

Column 2, line 51, "Disclosure of the Invention" should be a subheading

-- DISCLOSURE OF INVENTION -- for next paragraph.

Signed and Sealed this

Seventeenth Day of March, 1992

Attest:

HARRY F. MANBECK, JR.

*Attesting Officer*     *Commissioner of Patents and Trademarks*